(12) United States Patent
Mohammadi et al.

(10) Patent No.: US 11,291,618 B2
(45) Date of Patent: *Apr. 5, 2022

(54) LONG WEAR SKINCARE COMPOSITIONS

(71) Applicant: ELC Management LLC, Melville, NY (US)

(72) Inventors: Fatemeh Mohammadi, Hauppauge, NY (US); Sunni L. Tejada, Deer Park, NY (US); Lisa Qu, Flushing, NY (US); Anna Czarnota, Commack, NY (US); Tsung-Wei Robert Mou, Stony Brook, NY (US); Wilson A. Lee, Hauppauge, NY (US)

(73) Assignee: ELC Management LLC, Melville, NY (US)

( * ) Notice: Subject to any disclaimer, the term of this patent is extended or adjusted under 35 U.S.C. 154(b) by 238 days.

This patent is subject to a terminal disclaimer.

(21) Appl. No.: 16/816,995

(22) Filed: Mar. 12, 2020

(65) Prior Publication Data

US 2020/0289398 A1    Sep. 17, 2020

Related U.S. Application Data

(60) Provisional application No. 62/819,312, filed on Mar. 15, 2019.

(51) Int. Cl.

| | | |
|---|---|---|
| *A61K 8/81* | (2006.01) | |
| *A61K 8/04* | (2006.01) | |
| *A61K 8/06* | (2006.01) | |
| *A61Q 19/00* | (2006.01) | |
| *A61K 8/49* | (2006.01) | |
| *A61K 8/368* | (2006.01) | |
| *A61K 8/64* | (2006.01) | |
| *A61K 8/55* | (2006.01) | |
| *A61K 8/02* | (2006.01) | |

(52) U.S. Cl.
CPC .......... *A61K 8/8152* (2013.01); *A61K 8/0212* (2013.01); *A61K 8/042* (2013.01); *A61K 8/044* (2013.01); *A61K 8/062* (2013.01); *A61K 8/368* (2013.01); *A61K 8/4913* (2013.01); *A61K 8/4926* (2013.01); *A61K 8/4953* (2013.01); *A61K 8/55* (2013.01); *A61K 8/64* (2013.01); *A61Q 19/00* (2013.01); *A61K 2800/262* (2013.01); *A61K 2800/30* (2013.01)

(58) Field of Classification Search
CPC .................................................... A61Q 19/00
See application file for complete search history.

(56) References Cited

U.S. PATENT DOCUMENTS

| | | | |
|---|---|---|---|
| 2,949,403 | A | 8/1960 | Andreadis et al. |
| 4,708,865 | A | 11/1987 | Turner |
| 4,803,195 | A | 2/1989 | Holzner |
| 5,374,614 | A | 12/1994 | Behan et al. |
| 5,874,072 | A | 2/1999 | Alwattari et al. |
| 6,171,605 | B1 | 1/2001 | Bevacqua et al. |
| 6,403,109 | B1 | 6/2002 | Stora |
| 6,774,101 | B2 | 8/2004 | Stora et al. |
| 7,223,382 | B2 | 5/2007 | Sokolinsky et al. |
| 7,226,901 | B2 | 6/2007 | Stora |
| 7,323,162 | B2 | 1/2008 | Martin et al. |
| 7,655,613 | B2 | 2/2010 | Vlad et al. |
| 7,682,621 | B2 | 3/2010 | Lamberty et al. |
| 7,794,694 | B2 | 9/2010 | Giacomoni et al. |
| 7,846,889 | B2 | 12/2010 | Vlad et al. |
| 8,343,521 | B2 | 1/2013 | Shick et al. |
| 8,920,787 | B2 | 12/2014 | Li et al. |
| 8,932,570 | B2 | 1/2015 | Mu et al. |
| 9,072,686 | B2 | 7/2015 | Bui et al. |
| 9,078,835 | B2 | 7/2015 | Bui et al. |
| 9,301,910 | B2 | 4/2016 | Yontz |
| 10,813,874 | B2 * | 10/2020 | Lee .................. A61K 8/345 |
| 10,980,717 | B2 * | 4/2021 | Lee .................. A61K 8/8147 |
| 11,103,439 | B2 * | 8/2021 | Lee .................. A61Q 1/02 |
| 11,129,788 | B1 * | 9/2021 | Lee .................. A61K 8/368 |
| 2003/0186836 | A1 | 10/2003 | Dumanois et al. |
| 2004/0161435 | A1 | 8/2004 | Gupta |
| 2004/0209795 | A1 | 10/2004 | Vlad |
| 2005/0053567 | A1 | 3/2005 | Liu |
| 2015/0004115 | A1 | 1/2015 | Tan et al. |
| 2018/0369119 | A1 | 12/2018 | Lee |

FOREIGN PATENT DOCUMENTS

| | | | |
|---|---|---|---|
| FR | 2954155 B1 | 2/2012 | |
| FR | 2954152 B1 | 12/2012 | |

OTHER PUBLICATIONS

PCT International Search Report; International Application No. PCT/US2020/022391; Completion Date: Jun. 26, 2020; dated Jun. 29, 2020; 18.15.
PCT Written Opinion of the International Searching Authority; International Application No. PCT/US2020/022391; Completion Date: Jun. 26, 2020; dated Jun. 29, 2020; 18.15.

* cited by examiner

*Primary Examiner* — Gina C Justice
(74) *Attorney, Agent, or Firm* — Peter Giancana

(57) ABSTRACT

A cosmetic mask composition including a combination of acrylates/VA copolymer and acrylates copolymer. The cosmetic mask composition includes about 5% to 30% by weight of acrylates/VA copolymer, and about 0.2% to 2% by weight of acrylates copolymer. The ratio of acrylates/VA copolymer to acrylates copolymer is in the range of 15:1 to 25:1.

8 Claims, 2 Drawing Sheets

LONG WEAR SKINCARE COMPOSITIONS

FIELD OF THE INVENTION

The present invention relates to skincare compositions in the form of long wear face masks, including leave-on masks, peel-off masks, and invisible spray-on masks.

BACKGROUND

Existing facial peel-off masks often include polyvinylpyrrolidone (PVP) or polyvinyl alcohol (PVA), which can be uncomfortable, especially for consumers with sensitive skin. They are also difficult to remove. Many so-called leave-on masks, masks that are intended to be worn for an extended periods, such as eight hours, are not transfer resistant. This can be true of overnight treatment masks where transfer of product to a pillow, for example, is likely. It may also be true of masks that provide an aesthetic benefit, that are intended to be worn in public throughout the day.

In co-pending application, US2018-0369119 (incorporated herein, in its entirety, by reference), disclosed are specific combinations of acrylates/VA copolymer (20-30% by weight of total composition) and acrylates copolymer (0.5-2.5% by weight of total composition) in a cosmetically acceptable base or delivery vehicle. Such compositions were useful as high shine color cosmetic compositions that are flexible and resistant to water below about 43° C. The compositions wear well, are transfer, smudge and flake resistant, as well as oil resistant, making them very suitable as high shine, long wear cosmetics. One unique and advantageous feature of those compositions is that they are hydrophilic before and during use, but hydrophobic upon drying. This is unusual for a single phase aqueous cosmetic composition. Also, those compositions are easily removed when scrubbed with water above a certain temperature, but are difficult to remove with water below that temperature. This is unlike the present invention where additional refinement of the concentrations and ratio of the two polymers has led to additional uses and benefits. Mask compositions disclosed herein are transfer resistant and flexibility, may deliver mattifying or radiance effects, reduce trans-epidermal water loss (TEWL), and offer a vehicle for delivery of actives to the skin.

SUMMARY

Embodiments hereon provide a skincare composition including a combination of acrylates/VA copolymer and acrylates copolymer. The skincare composition includes about 5% to 30% by weight of acrylates/VA copolymer, and about 0.2% to 2% by weight of acrylates copolymer. The ratio of acrylates/VA copolymer to acrylates copolymer is in the range of 15:1 to 25:1. Often these compositions will be single-phase, but emulsions are also possible. The composition can be in the form of cream, lotion, gel, serum or spray-on mask. The mask may be invisible upon drying.

DETAILED DESCRIPTION

Figure 1:
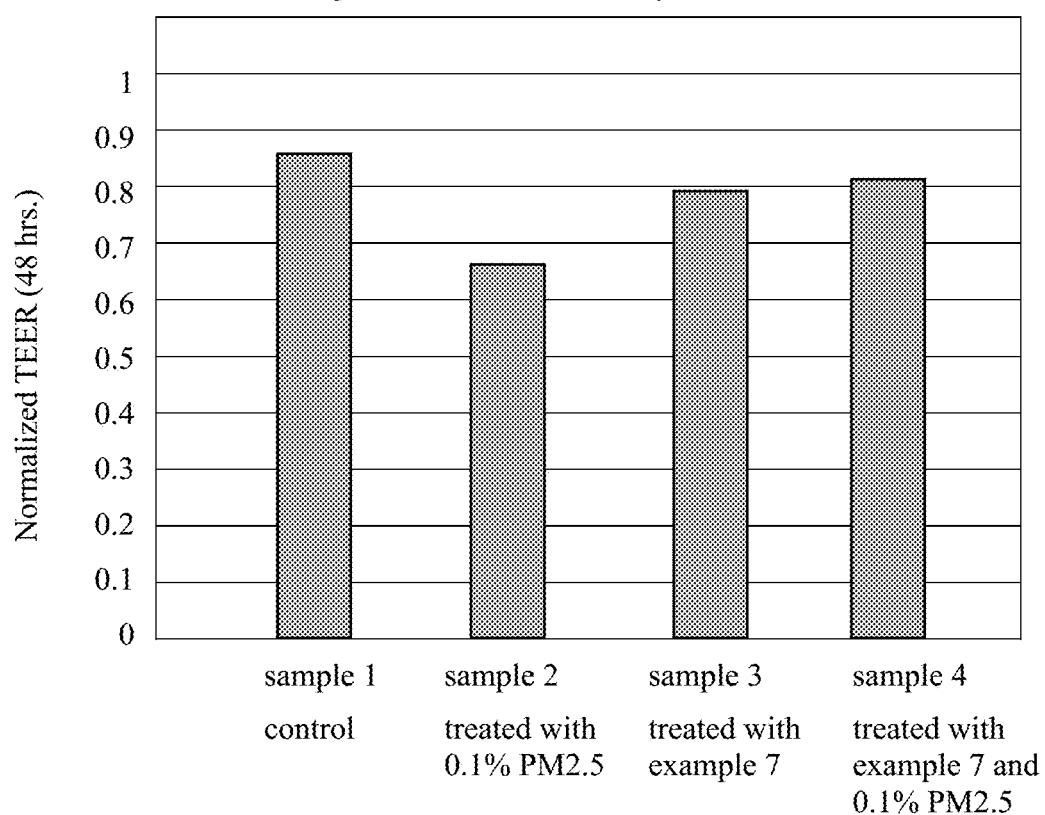
FIG. 1 is a graph of the effect of the composition of Example 7 on PM2.5 measured by TEER skin models.

Except in operating and comparative examples, or where otherwise explicitly indicated, all numbers in this description indicating amounts or ratios of material or conditions of reaction, physical properties of materials and/or use are to be understood as modified by the word "about." All amounts are presented as percentages by weight of the final composition, unless otherwise specified.

Throughout the present specification, "film former" or the like refers to a polymer leaves a film on the substrate to which it is applied, for example, after a solvent accompanying the film former has evaporated, absorbed into and/or dissipated on the substrate.

"Transfer resistant" or "transfer proof" as used herein refers to compositions that are not readily removed by contact with another material, such as clothing or water. Transfer resistance may be evaluated by any method known in the art. For example, a composition may be evaluated based on the amount of product transferred from the skin or hair of a wearer to any other substrate, such as clothing. For example, a composition may be transfer resistant if a majority of the product is left on the wearer's skin or hair. Further, the amount transferred may be compared with that transferred by other compositions, such as commercially available compositions.

As used herein, "good wear" or "long wear" refer to compositions that maintain adhesion to skin after curing.

A "flexible" composition is one that when applied to the skin for its intended use, does not crack or flake for a defined period of time, such as four hours or eight hours or more of wear. If a composition is not adequately flexible, then it is "rigid".

By "single phase" it is intended that the composition is in a stable homogeneous form rather than in the form of a heterogeneous water-in-oil or oil-in-water emulsion.

"Comprising" and the like, mean that a list of elements may not be limited to those explicitly recited.

Compositions herein comprise specific combinations of acrylates/VA copolymer and acrylates copolymer in a cosmetically acceptable aqueous base or delivery vehicle. Many water soluble ingredients are easily incorporated into the compositions with no adverse effect on the compositions basic performance. Compositions herein are applied in a hydrophilic state, dry to a hydrophobic state. and are easily removed with water and shear, or peeled off with or without water. The compositions are easy to manufacture.

Acrylates/VA Copolymer

A first main ingredient of the invention is acrylates/VA copolymer (INCI name), $C_{15}H_{26}O_4$, also known as ethenyl acetate or 2-ethylhexyl prop-2-enoate (IUPAC names); CAS number 25067-02-1. For detailed information, see PubChem Compound Database; CID=168269.

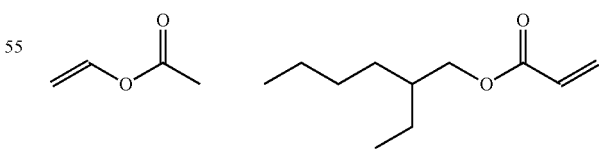

In cosmetics, this material often functions as a binder, film former, adhesive, and/or hair fixative. When deployed in aqueous cosmetic systems acrylates/VA copolymer can impart a film on the skin or hair. The pure acrylates/VA copolymer film features a temperature dependence, such that a water rinse of about 40° C. or more will degrade the film, and allow it to be removed easily from a surface, while retaining its integrity at temperatures at or below normal skin temperature (i.e. 36.5-37.5° C.).

Embodiments herein typically comprise 5% to 30% of acrylates/VA copolymer by total weight of the composition. Acrylates/VA copolymer is commercially available, for example, as Vinysol 2140L, and Vinysol 2140LH from Daido Chemical Corp. Both the Vinysol 2140L and the Vinysol 2140LH include a 46.6% aqueous mixture of acrylates/VA copolymer. Therefore, when using Vinysol 2140L or Vinysol 2140LH, in order to achieve the concentrations of acrylates/VA copolymer noted above, the concentration of Vinysol 2140L and/or Vinysol 2140LH should be about 10.7% to 64.4%, for example 15%-60%, for example 20%-55%, for example 25%-50% by total weight of the composition. For mask products of the present invention, the upper end (50%-60%) and lower end (15%-20%) of the broad range have proved particularly useful, depending on the use and the effect sought.

Vinysol 2140L is reported to have a pH of 4.5, a viscosity of 2,000 mPa-s, a calculated glass transition temperature $(T_g)$ of −9° C., while the film exhibits a break elongation of 1,200%, and a break strength of 1.2 MPa (when spread to a thickness 0.1 mm). The strength of the material makes it suitable for thinly applied, leave-on cosmetics that will not crack or flake easily. However, at the relatively high concentrations, prototype formulations were too rigid or aesthetically uncomfortable to be commercially useful. The task was to increase the flexibility and comfort of application of the composition without jeopardizing the beneficial properties of the cosmetic system (e.g., enhanced actives delivery, hydrophilicity when wet, hydrophobicity when dry, good wear, etc.).

Acrylates Copolymer

Embodiments herein combine the acrylates/VA copolymer described above with an acrylates copolymer that has a lower $T_g$ than acrylates/VA copolymer, which serves to address the problem of high rigidity associated with using acrylates/VA copolymer alone. In general, a lower $T_g$ provides more flexibility to the resulting mask. It also makes the composition tackier and have a longer dry time, but in the present invention a longer dry time can be desirable. By itself, acrylates/VA copolymer dries too quickly to be useful in a consumer environment, where time for application and grooming is needed. However, a composition that takes too long to dry (e.g., over 20 minutes or over 30 minutes) is also not commercially desirable. Embodiments herein provide a suitable dry time, and the right amount of flexibility in the dried composition, by utilizing a second main ingredient which is acrylates copolymer, $C_{14}H_{22}O_6$, also known as ethyl prop-2-enoate; methyl 2-methylprop-2-enoate or 2-methylprop-2-enoic acid (IUPAC names); CAS number 25133-97-5. For detailed information, see PubChem Compound Database; CID=168299. In various types of cosmetic formulations, acrylates copolymer has a wide variety of uses including as film formers, hair fixatives, binders, and suspending agents, viscosity enhancers, antistatic agents and adhesives. At concentrations and ratios discussed herein, the combination of acrylates/VA copolymer and acrylates copolymer has a dry time that is suitable for the consumer, while the increase in tackiness is considered acceptable for consumer use.

In embodiments herein, useful concentrations of acrylates copolymer are from 0.2% to 2% based on total weight of the composition; for example 0.33%-1.2%. Acrylates copolymer is commercially available, for example, as Daitosol 5000AD from Daito Kasei Kogyo Co. Daitosol 5000AD is a 50% aqueous mixture of acrylates copolymer, Therefore, in order to achieve the concentrations of acrylates copolymer noted above, the concentration of Daitosol 5000AD should be about 0.4%-4%, for example 0.75%-3%, for example 1.0%-2.5% by total weight of the composition. Daitosol 5000AD is reported to have a pH of 5.5-7.5, a viscosity of 50-100 mPa-s, a glass transition temperature $(T_g)$ of about −14° C.

Accordingly, embodiments herein typically comprise 5% to 30% of acrylates/VA copolymer by total weight of the composition, and about 0.2% to 2% of acrylates copolymer by weight of the composition. Furthermore, within those ranges, we have found excellent results when the ratio of the acrylates/VA copolymer to acrylates copolymer in composition described herein is in the range of 15:1 to 25:1, preferably 18:1 to 22:1, most preferably 20:1.

Forms of the Compositions

Embodiments of the invention may typically be water suspensions, gel suspensions or water-in-oil emulsions. All compositions of the invention are applied to the skin and allowed to dry (e.g., for five minutes to twenty minutes), to form a mask.

The gel suspensions and emulsions will typically be serums and lotions. When it is desired to remove the mask, the mask may be removed from the skin in one or a few continuous sheets. Application of water may aid in this process. The use of water will disrupt the skin adhesion while maintaining film integrity so the mask will peel off in one sheet or just a few sheets, comfortably, without stripping the skin. Advantageously, the peel-off masks herein are aqueous peel-off masks that are free of polyvinylpyrrolidone (PVP) or polyvinyl alcohol (PVA).

Transparent, Invisible Spray-On Mask

The water suspension embodiments of the invention, at the lower end of the concentration ranges of the polymer blend (less than about 10% acrylates/VA copolymer), are particularly suitable as spray-on products that dry to form an invisible mask. The compositions are sufficiently shearable, even without the aid of a plasticizer or thinning agent. "Sufficiently shearable" means that they can be sprayed by the types of spray systems that are common in the cosmetic and personal care industries. These masks are very thin and light weight, and will rinse off with soap, warm water and shear, not necessarily in sheets.

In some embodiments of the invention, a spray is useful to provide a light-weight mask that acts as a shield against environmental aggressors. After spraying on the skin, the dried mask can act as a physical barrier to protect the skin against fine particles having a diameter of 2.5 or less (so called, PM 2.5), and protects the skin against TEWL. Data on these effects in presented below.

In other embodiments of the invention, a spray is useful to provide a radiant glow to the skin without the use of optic pearls. After spraying on the skin, the product dries to a transparent film that is able to scatter light, giving a natural radiance effect without the use of traditional cosmetic pearl materials. Because the dried product is transparent and very clear, the product may be applied over makeup to create a radiant finish, while also helping to set the makeup in place.

Mattifying Effect Mask

In other embodiments, a product that can allow the consumer to have a perfected/blurred finish to skin, that is comfortable and lasts for at least eight hours can be achieved using the copolymer blend described herein. As noted above, the combination of acrylates/VA copolymer and acrylates copolymer, as described herein, naturally provides a high shine finish. However, we have discovered that the addition of sodium polyacrylate (available commercially as Kobogaurd® SP from Kobo Products, for example) to the composition containing the copolymer blend overcomes or mutes the high shine characteristic of the copolymer blend without significantly affecting its other useful properties as described herein. The concentration of sodium polyacrylate should be adjusted between about 0.1% and 5.0%, by weight of the composition, to achieve the desired degree of mattifying effect. Addition of the sodium polyacrylate creates a skincare gel formula which gives a matte/perfected look to skin, while still providing a long wear product. Advantageously, the matte/blurred effect to skin can be achieved without the addition of powders which are traditionally used in order to give a matte/blurred effect to skin.

Actives

Embodiments herein may be used as overnight treatment products to provide delivery of active ingredients to the skin. Using the combination of polymers as described herein, the compositions eliminate the need for surface engineering, molecular modification or encapsulation. Exemplary actives include, but are not limited to, niacinamide, caffeine, vitamin C and vitamin C derivatives (ascorbic acid, sodium ascorbyl phosphate, ascorbyl palmitate, retinyl ascorbate, tetrahexyldecyl ascorbate, magnesium ascorbyl phosphate, ascorbyl glucoside, etc.), alpha glucosyl hesperidin, and any other suitable water-soluble actives. Oil soluble actives, such as vitamin A (i.e. retinyl palmitate), and vitamin E (i.e. tocopheryl acetate), may also be included in embodiments herein for enhanced actives delivery. Alpha-hydroxy-acids, beta-hydroxy-acids and peptides may also be included.

EXAMPLES

In the following examples, Vinysol 2140L is a 46.6% aqueous mixture of acrylates/VA copolymer. Daitosol 5000AD is 50% aqueous mixture of acrylates copolymer.

Example 1: Peel-Off Mask

| Sequence | INCI Name | Percent |
|---|---|---|
| 1 | water | 11.27 |
| 1 | hydroxyacetophenone | 0.50 |
| 1 | propanediol | 1.00 |
| 2 | Vinysol 2140L | 60.00 |
| 2 | Daitosol 5000AD | 3.00 |
| 3 | alcohol denat. | 3.00 |
| 4 | xanthan gum | 0.30 |
| 4 | propanediol | 2.63 |
| 5 | kaolin | 15.00 |
| 6 | charcoal powder | 3.00 |
| 7 | ethylhexylglycerin | 0.30 |
| | TOTAL: | 100.00 |

The sequences above were combined in a manner known to one skilled in the art to form a gel suspension.

Example 2: Face Mask with Actives

| Sequence | INCI Name | Percent |
|---|---|---|
| 1 | water | 31.85 |
| 1 | disodium EDTA | 0.05 |
| 1 | caffeine | 0.20 |
| 2 | butylene glycol | 1.00 |
| 2 | xanthan gum | 0.30 |
| 3 | glycerin | 0.50 |
| 3 | butylene glycol | 1.00 |
| 3 | ammonium acryloyldimethyltaurate/VP copolymer | 0.60 |
| 4 | alcohol denat. | 5.00 |
| 4 | propanediol | 2.00 |
| 4 | caprylyl glycol | 0.30 |
| 4 | phenoxyethanol | 0.60 |
| 5 | Vinysol 2140L | 50.00 |
| 5 | Daitosol 5000AD | 2.50 |
| 5 | bismuth oxychloride | 4.00 |
| 6 | sodium hydroxide | 0.10 |
| | TOTAL: | 100.00 |

The sequences above were combined in a manner known to one skilled in the art to form a gel suspension.

Example 3: Invisible Spot Treatment Mask

| Sequence | INCI Name | Percent |
|---|---|---|
| 1 | water | 33.83 |
| 1 | disodium EDTA | 0.05 |
| 2 | glycerin | 1.00 |
| 2 | butylene glycol | 1.00 |
| 2 | xanthan gum | 0.30 |
| 3 | phenoxyethanol | 0.50 |
| 3 | ethylhexylglycerin | 0.30 |
| 4 | salicylic acid | 0.50 |
| 4 | alcohol denat. | 5.00 |
| 5 | sodium hydroxide | 0.02 |
| 5 | water | 5.00 |
| 5 | Vinysol 2140L | 50.00 |
| 5 | Daitosol 5000AD | 2.50 |
| | TOTAL: | 100.00 |

The sequences above were combined in a manner known to one skilled in the art to form a gel suspension.

Example 4: Overnight Tone-Up Mask

| Sequence | INCI Name | Percent |
|---|---|---|
| 1 | water | 21.34 |
| 1 | disodium EDTA | 0.05 |
| 1 | caffeine | 0.20 |
| 2 | butylene glycol | 1 |
| 2 | phenoxyethanol | 0.50 |
| 2 | ethylhexylglycerin | 0.30 |
| 3 | niacinamide | 1.00 |
| 3 | glucosyl hesperidin | 0.10 |
| 4 | water | 2.50 |
| 4 | 3-O-ethyl ascorbic acid | 1.00 |
| 4 | sodium hydroxide | 0.01 |
| 5 | Vinysol 2140L | 20.00 |
| 5 | Daitosol 5000AD | 1.00 |
| 6 | propanediol | 1.00 |
| 6 | PEG-12 dimethicone/PPG-20 crosspolymer/caprylyl | 47.50 |

-continued

| Sequence | INCI Name | Percent |
|---|---|---|
|  | methicone |  |
| 6 | tocopheryl acetate | 0.50 |
| 6 | glycerin | 2.00 |
|  | TOTAL: | 100.00 |

The sequences above were combined in a manner known to one skilled in the art to form a gel suspension.

Example 5: Eye Mask

| Sequence | INCI Name | Percent |
|---|---|---|
| 1 | water | 57.48 |
| 1 | disodium EDTA | 0.05 |
| 1 | caffeine | 0.20 |
| 2 | butylene glycol | 1 |
| 2 | glycerin | 1 |
| 2 | carbomer/polyphosphorylcholine glycol acrylate/water | 0.1 |
| 3 | propanediol | 1.00 |
| 3 | phenoxyethanol | 0.40 |
| 3 | ethylhexylglycerin | 0.30 |
| 4 | sodium dehydroacetate | 0.07 |
| 5 | glycerin | 1 |
| 5 | xanthan gum | 0.30 |
| 6 | Vinysol 2140L | 20.00 |
| 6 | Daitosol 5000AD | 1.00 |
| 7 | niacinamide | 1.00 |
| 7 | glucosyl hesperidin | 0.10 |
| 8 | water | 2.50 |
| 8 | 3-O-ethyl ascorbic acid | 0.50 |
| 8 | sodium hydroxide | 0.01 |
| 9 | tocopheryl acetate | 0.50 |
| 9 | *carthamus tinctorius* (safflower) oleosomes/water | 7.00 |
| 9 | squalene | 4.50 |
|  | TOTAL: | 100.00 |

The sequences above were combined in a manner known to one skilled in the art to form an oil-in-water emulsion.

Example 6: Mattifying Mask

| Sequence | INCI Name | Percent |
|---|---|---|
| 1 | water | 23.65 |
| 1 | Vinysol 2140L | 60.00 |
| 1 | Daitosol 5000AD | 3.00 |
| 2 | phenoxyethanol/chloroxylenol | 0.85 |
| 3 | dimethicone/vinyl dimethicone crosspolymer/laureth-9/water | 10.00 |
| 4 | sodium polyacrylate | 2.00 |
| 4 | sodium polyacrylate/silica | 0.50 |
|  | TOTAL PERCENT: | 100.00 |

The sequences above were combined in a manner known to one skilled in the art to form a gel suspension.

Example 7: Radiance Spray

| Sequence | INCI Name | Percent |
|---|---|---|
| 1 | water | 80.40 |
| 1 | Vinysol 2140L | 15.00 |
| 1 | Daitosol 5000AD | 0.75 |
| 1 | alcohol denat. | 3.00 |
| 1 | phenoxyethanol/chloroxylenol | 0.85 |
|  | TOTAL PERCENT: | 100.00 |

The sequences above were combined in a manner known to one skilled in the art to form a water suspension, which is a sprayable composition.

Example 8: Actives Delivery Base for Testing

| Sequence | INCI Name | Percent |
|---|---|---|
| 1 | water | 69.90 |
| 2 | butylene glycol | 1.00 |
| 2 | xanthan gum | 0.3 |
| 3 | propanediol | 4.00 |
| 3 | ethylhexylglycerin | 0.30 |
| 3 | phenoxyethanol | 0.50 |
| 4 | Vinysol 2140L | 20.00 |
| 4 | Daitosol 5000AD | 1.00 |
| 4 | alcohol denat. | 3.00 |
| 4 | **active ingredient |  |
|  | TOTAL PERCENT: | 100.00 |

**see Table 1 below for exemplary actives and concentrations.

The sequences above were combined in a manner known to one skilled in the art to form a gel suspension.

Experimental Data and Results

Actives Delivery Test

Using the actives delivery base shown in Example 8 above, three hydrophilic actives were tested in the base with and without the copolymer blend described herein (e.g., combination of acrylates/VA copolymer and acrylates copolymer). The placebo formulas differed from Example 8 in that the copolymer blend was removed from the base and Q.S. with water.

TABLE 1

Actives Added to Example 8 Base

| Formula # | Active (total weight of composition) | Copolymer Blend (total weight of composition) | Active Log P |
|---|---|---|---|
| 1 | caffeine at 0.5% | 21% | −0.1 |
| 1P (placebo) |  | 0% |  |
| 2 | niacinamide at 2.0% | 21% | −0.4 |
| 2P (placebo) |  | 0% |  |
| 3 | ascorbyl glucoside (AA2G) at 2.0% | 21% | −4.79 |
| 3P (placebo) |  | 0% |  |

Method

In this study, exemplary actives with different hydrophilicity value were chosen. P is the partition coefficient, where a smaller P (more negative log P) indicates greater hydrophilicity. A penetration test was performed using a Strat-M® membrane, and the collected sample was then analyzed by Ultra-Performance Liquid Chromatography (UPLC). In the receptor chamber of a Franz Cell, 5.00 mL of the incubation medium was added as the collection phase. A Strat-M® membrane was loaded on top of the receptor chamber. The donor chamber was then added on top of the Strat-M® membrane, 0.80 mL of the crème was added to the donor chamber. The Franz Cell was left under room temperature for 48 hours (e.g., for AA2G and caffeine) or 72 hours (e.g., niacinamide). At the end of that time period, 1.00 mL of the collection phase was withdrawn from the sampling port as the sample solution. The sample solution was filtered through a 0.45 micrometer (μm) syringe filter and then added into a 2.0 milliliter (mL) High Performance Liquid Chromatography (HPLC) vial. ACQUITY H UPLC from the Waters Corporation was used to analyze the collected samples from the Franz Cell study. The UPLC parameters are shown in Table 2 below.

TABLE 2

UPLC study parameters.

| Active | AA2G | Caffeine and Niacinamide |
|---|---|---|
| Column | XSelect HSS T3 2.5 um 3.0*50 mm Column XP | |
| Mobile Phase | 95% DI water, 5% of 0.1% Formic Acid in Acetonitrile | 60% DI water, 40% of 0.1% Formic Acid in Acetonitrile |
| Flow rate | 0.80 mL/min | |
| Column Temp (° C.) | 40 | |
| Injection volume (μl) | 2 | |
| Detection wavelength (nm) | 254 | |

Results and Discussion

The amount of actives in the collection phase were analyzed by UPLC following the method described above. The data is summarized in Table 3 below.

TABLE 3

Penetration study results.

| Formula # | Active | Penetrated Active Concentration (ppm) | % of Penetration |
|---|---|---|---|
| 1 | Caffeine 0.5% | 1290 | 161 |
| 1P (placebo) | | 856 | 107 |
| 2 | Niacinamide, 2.0% | 54 | 1.7 |
| 2P | | 618 | 19.3 |
| 3 | AA2G 2.0% | 1103 | 34.5 |
| 3P | | 44 | 1.4 |

The percentage penetration of caffeine is greater than 100%, which means there are some interference molecules in the system which were not separated from caffeine. As shown above, the inclusion of the copolymer blend enhanced the delivery of AA2G, which is very hydrophilic according to the Log P value. Niacinamide is much less hydrophilic, and the copolymer blend did not enhance the delivery of this active ingredient. The addition of the copolymer blend appears to enhance the delivery of hydrophilic actives into the skin.

Film Integrity Test

Variations of the formula shown in Example 6 were tested, wherein the concentration of acrylates/VA copolymer was varied, while the level of acrylates copolymer was held constant. These are shown in Table 4.

Method

The integrity the cured film of the compositions was determined by measuring contact angle, bending force and adhesion. A texture analyzer (available as the TA XT Plus from Texture Technologies Corp.), and a goniometer (contact angle instrument available from Future Digital Scientific) were used. Contact angle measures hydrophobicity (water repelling). The greater the contact angle, the more hydrophobic the film. Bending force represents elasticity and flexibility of the dried film, which directly affect comfort of wear. Adhesion represents duration of wear. The results of these tests are shown in Table 4.

TABLE 4

Test Results of Mattifying Compositions

| Sample | | Contact Angle | Bending Force | Adhesion |
|---|---|---|---|---|
| 1 | example 6 base with no copolymer blend (control) | 35° | 0.1 g | 60 g |
| 2 | example 6 base with 5% Vinysol 2140L 3% Daitosol 5000AD | 55° | 0.3 g | 600 g |
| 3 | example 6 base with 30% Vinysol 2140L 3% Daitosol 5000AD | 65° | 0.4 g | 1,500 g |
| 4 | example 6 base with 60% Vinysol 2140L 3% Daitosol 5000AD | 69° | 1.9 g | 2,200 g |

The best performing formula was sample 4, with 60% Vinysol 2140L (27.96% acrylates/VA copolymer) and 3% Daitosol 5000AD (1.5% acrylates copolymer) (18.64:1 ratio), by total weight of the composition. When dried, this formula demonstrated the highest bending force, adding to the comfort, and the greatest adhesion, making it the best option for long wear. It was also the most hydrophobic, making it most resistant to unintentional degradation by moisture. The next best performer was sample 3, with 30% Vinysol 2140L and 3% Daitosol 5000AD. In this composition, the ratio of acrylates/VA copolymer to acrylates copolymer was 9.3, and there was a really significant drop off in bending force and adhesion, suggesting that this ratio is not useful for the uses described herein. When wetted, all test films peeled cleanly, in one or a few sheets, from a glass substrate.

Barrier Properties Test

The composition shown in Example 7 was tested for pollution protection against fine particulate matter (PM 2.5) and trans-epidermal water loss (TEWL). The trans-epidermal electrical resistance (TEER) and TEWL levels in skin models were measured over 48 hours and the experimental results are shown in FIG. 1 and FIG. 2, respectively.

In FIG. 1, a higher TEER value indicates a more effective barrier. The control skin model (sample 1) was not exposed to the formula of example 7, nor to PM2.5. The sample 2 skin model was exposed to 0.1% 2.5 PM for 48 hours, and the TEER value dropped significantly compared to the control sample, indicating poor barrier function. The sample 3 skin model was treated with the formula of example 7, but not exposed to 2.5 PM for 48 hours, and the sample 4 skin model was both treated with the formula of example 7, and exposed to 0.1% 2.5 PM for 48 hours. Sample 3 had a decrease in TEER value compared to the control, but it was within the experimental error. Sample 4 had a TEER value that is statistically the same as sample 3, which indicates that the formula of example 7 formed a highly effective barrier against PM2.5. The formula of example 7 has a relatively low level (7%) of acrylates/VA copolymer and 0.375% acrylates copolymer, so embodiments of the present composition with even higher concentrations are expected to perform at least as well as a barrier against 2.5 PM.

Figure 2:
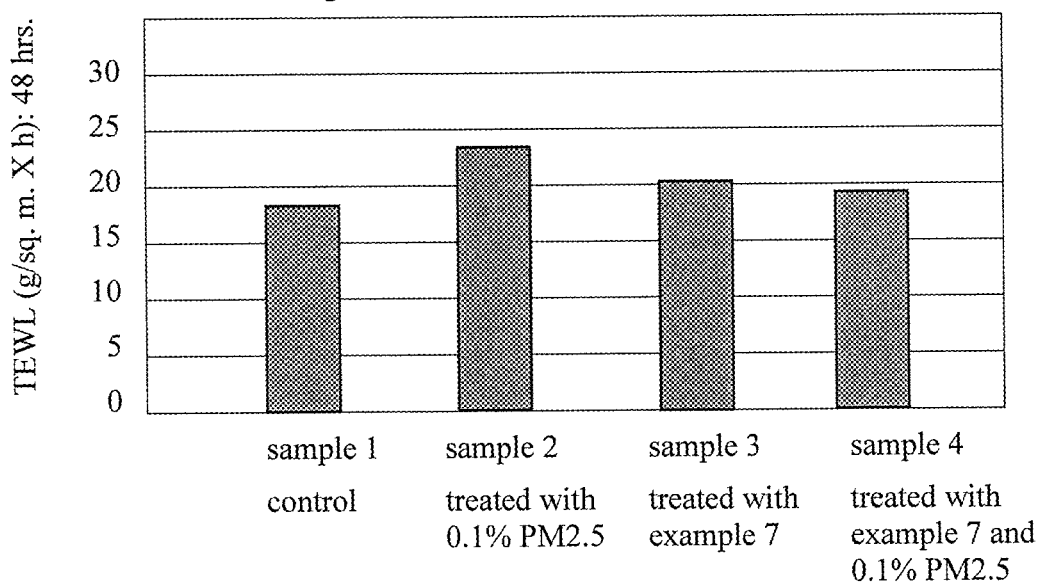
FIG. 2 is a graph of the effect of the composition of Example 7 on PM2.5 measured by TEWL skin models.

In FIG. 2, a lower TEWL value indicates a more effective barrier. The control skin model (sample 1) was not exposed to the formula of example 7, nor to PM2.5. The sample 2 skin model was exposed to 0.1% 2.5 PM for 48 hours, and the TEWL increased significantly compared to the control sample, indicating poor barrier function. The sample 3 skin model was treated with the formula of example 7, but not exposed to 2.5 PM for 48 hours, and the sample 4 skin model was both treated with the formula of example 7, and exposed to 0.1% 2.5 PM for 48 hours. Sample 3 showed a increase in TEWL compared to the control, but it was within the experimental error. Sample 4 had a TEWL value that is statistically the same as sample 3, which indicates that the formula of example 7 formed a highly effective barrier against PM2.5.

These results show that the composition of Example 7 protects against water loss and aids in barrier function against PM2.5.

It will be appreciated and should be understood that the exemplary embodiments of the invention described above can be carried out in a number of different ways. Given the teachings of the invention provided herein, one of ordinary skill in the related art will be able to contemplate other implementations of the invention. Indeed, although illustrative embodiments of the present invention have been described herein with reference to the accompanying examples, it is to be understood that the invention is not limited to those precise embodiments, and that various other changes and modifications may be made by one skilled in the art without departing from the scope of the invention.

What is claimed is:

1. A cosmetic mask composition comprising 5% to 30% by weight of acrylates/VA copolymer, and 0.2% to 2% by weight of acrylates copolymer, wherein the ratio of acrylates/VA copolymer to acrylates copolymer is in the range of 15:1 to 25:1.

2. The cosmetic mask composition of claim 1, wherein the ratio of acrylates/VA copolymer to acrylates copolymer is in the range of 18:1 to 22:1.

3. The cosmetic mask composition of claim 1, wherein the acrylates copolymer is in the range of 0.33% to 1.2% by weight of the total composition.

4. The cosmetic mask composition of claim 1, wherein the composition is in the form of an oil-in-water emulsion or a gel suspension.

5. The cosmetic mask composition of claim 1, wherein the composition is in the form of water suspension.

6. The cosmetic mask composition of claim 5 wherein the skincare composition is applied as a spray.

7. The cosmetic mask composition of claim 1, further comprising at least one active ingredient selected from ascorbic acid, sodium ascorbyl phosphate, ascorbyl palmitate, retinyl ascorbate, tetrahexyldecyl ascorbate, magnesium ascorbyl phosphate, and ascorbyl glucoside.

8. The cosmetic mask composition of claim 1, further comprising at least one active ingredient selected from salicylic acid, retinyl palmitate, niacinamide, caffeine, alpha-hydroxy acids, and peptides.

* * * * *